US012569883B2

(12) United States Patent

Hatakeyama

(10) Patent No.:     US 12,569,883 B2

(45) Date of Patent:     Mar. 10, 2026

(54) MULTILAYER BOARD, PROBE UNIT, AND ULTRASOUND ENDOSCOPE

(71) Applicant: OLYMPUS CORPORATION, Tokyo (JP)

(72) Inventor: Tomoyuki Hatakeyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 812 days.

(21) Appl. No.: 17/969,943

(22) Filed: Oct. 20, 2022

(65) Prior Publication Data

US 2023/0052510 A1     Feb. 16, 2023

Related U.S. Application Data

(63) Continuation of application No. PCT/JP2020/018047, filed on Apr. 27, 2020.

(51) Int. Cl.
*B06B 1/00*     (2006.01)
*A61B 8/00*     (2006.01)
*B06B 1/02*     (2006.01)
*B06B 1/06*     (2006.01)

(52) U.S. Cl.
CPC .............. *B06B 1/06* (2013.01); *A61B 8/4483* (2013.01); *B06B 1/0207* (2013.01); *A61B 8/4444* (2013.01); *B06B 2201/20* (2013.01); *B06B 2201/55* (2013.01); *B06B 2201/76* (2013.01)

(58) Field of Classification Search
CPC ..... B06B 1/06; B06B 1/0207; B06B 2201/20; B06B 2201/55; B06B 2201/76; B06B 1/0622
See application file for complete search history.

(56) References Cited

U.S. PATENT DOCUMENTS

| | | | | |
|---|---|---|---|---|
| 11,903,604 | B2 * | 2/2024 | Toda .............. | A61B 17/320068 |
| 2005/0255303 | A1 | 11/2005 | Sawatari et al. | |
| 2008/0196932 | A1 | 8/2008 | Sawatari et al. | |
| 2016/0372848 | A1 | 12/2016 | Yamada | |
| 2019/0090857 | A1 | 3/2019 | Yamamoto et al. | |

FOREIGN PATENT DOCUMENTS

| | | |
|---|---|---|
| CN | 1691871 A | 11/2005 |
| JP | 2006167282 A | 6/2006 |
| JP | 4812050 B2 | 11/2011 |
| WO | 2015141800 A1 | 9/2015 |

OTHER PUBLICATIONS

International Search Report dated Jul. 28, 2020 received in PCT/JP2020/018047.
Chinese Office Action dated Mar. 14, 2025 received in 202080100227.7.

* cited by examiner

*Primary Examiner* — Julio C. Gonzalez

(74) *Attorney, Agent, or Firm* — Scully, Scott, Murphy & Presser, P.C.

(57)     ABSTRACT

A multilayer board includes: a front-side layer; an intermediate layer; a back-side layer; the front-side layer; a first ground terminal and a second ground terminal for connecting ground lines of a plurality of shield lines to be connected to the multilayer board; a plurality of signal line connecting terminal arrays each including a plurality of signal line connecting terminals for connecting respective signal lines of the shield lines; and a wire having a thermal conductivity, the wire extending to the second end on the intermediate layer.

13 Claims, 19 Drawing Sheets

MULTILAYER BOARD, PROBE UNIT, AND ULTRASOUND ENDOSCOPE

CROSS-REFERENCE TO RELATED APPLICATION

This application is a continuation of International Application No. PCT/JP2020/018047, filed on Apr. 27, 2020, the entire contents of which are incorporated herein by reference.

BACKGROUND

1. Technical Field

The present disclosure relates to a multilayer board, a probe unit, and an ultrasound endoscope.

2. Related Art

In the medical field and the industrial field, an ultrasound endoscope is widely used for various kinds of examinations. A medical ultrasound endoscope includes an ultrasound transducer that is arranged on a distal end of an insertion portion that is inserted into a subject, such as a patient, and acquires an in-vivo image of the subject by ultrasound waves.

In the medical ultrasound endoscope, a technology for reducing a size and a diameter of the distal end of the insertion portion has been proposed to reduce a burden on a patient or the like. For example, in Japanese Patent No. 4812050, a diameter of a distal end of an insertion portion is reduced by connecting a cable in a shifted manner in a length direction to a flexible board that is connected to an ultrasound transducer.

SUMMARY

In some embodiments, a multilayer board includes: a front-side layer; an intermediate layer; a back-side layer; the front-side layer, the intermediate layer, and the back-side layer being laminated in a lamination direction of the multilayer board; the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board; a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively; a plurality of signal line connecting terminal arrays each including a plurality of signal line connecting terminals for connecting respective signal lines of the shield lines, the plurality of signal line connecting terminal arrays forming a part of the front-side layer and a part of the back-side layer in a vicinity of the ground terminal in the longitudinal direction, the plurality of signal line connecting terminal arrays being arranged along the longitudinal direction; and a wire having a thermal conductivity, the wire extending to the second end on the intermediate layer.

In some embodiments, a probe unit includes a plurality of shield lines, and a multilayer board. The multilayer board includes: a front-side layer; an intermediate layer; a back-side layer; the front-side layer, the intermediate layer, and the back-side layer being laminated in a lamination direction of the multilayer board; the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board; a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively; a plurality of signal line connecting terminal arrays each including a plurality of signal line connecting terminals for connecting respective signal lines of the shield lines, the plurality of signal line connecting terminal arrays forming a part of the front-side layer and a part of the back-side layer in a vicinity of the ground terminal in the longitudinal direction, the plurality of signal line connecting terminal arrays being arranged along the longitudinal direction; and a wire having a thermal conductivity, the wire extending to the second end on the intermediate layer.

In some embodiments, an ultrasound endoscope comprising an ultrasound transducer configured to transmit and receive ultrasound waves, a plurality of shield lines, and a multilayer board. The multilayer board includes: a front-side layer; an intermediate layer; a back-side layer; the front-side layer, the intermediate layer, and the back-side layer being laminated in a lamination direction of the multilayer board; the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board; a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively; a plurality of signal line connecting terminal arrays each including a plurality of signal line connecting terminals for connecting respective signal lines of the shield lines, the plurality of signal line connecting terminal arrays forming a part of the front-side layer and a part of the back-side layer in a vicinity of the ground terminal in the longitudinal direction, the plurality of signal line connecting terminal arrays being arranged along the longitudinal direction; and a wire having a thermal conductivity, the wire extending to the second end on the intermediate layer.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is an enlarged view of a board;

FIG. 7 is an enlarged view of a board;

FIG. 8 is an enlarged view of a board;

FIG. 10 is a partial projection view of the flexible board;

FIG. 14 is an enlarged view of the connection portion between the cable group and the flexible board;

DETAILED DESCRIPTION

Embodiments of a multilayer board, a probe unit, and an ultrasound endoscope according to the disclosure will be described below with reference to the drawings. The disclosure is not limited by the embodiments below. The disclosure is applicable to a general multilayer board, a general probe unit, and a general ultrasound endoscope.

Further, in description of the drawings, the same or corresponding components are appropriately denoted by the same reference symbols. Furthermore, it is necessary to note that the drawings are schematic, and dimensional relations among the components, ratios among the components, and the like may be different from actual ones. Moreover, the drawings may include portions that have different dimensional relations or ratios.

First Embodiment

Configuration of Endoscope System

Figure 1:
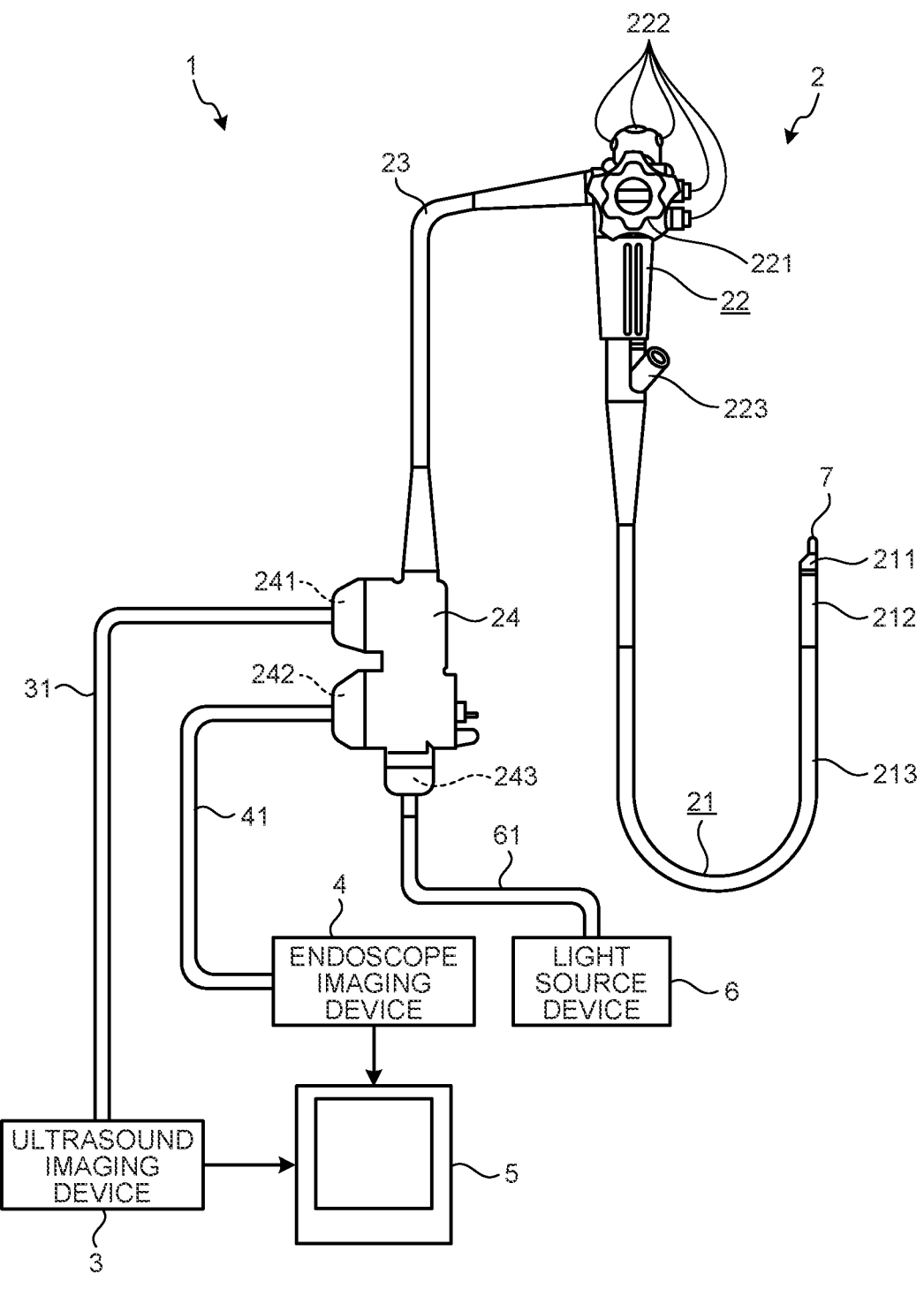
FIG. 1 is a diagram schematically illustrating an entire endoscope system including a multilayer board according to a first embodiment.

FIG. 1 is a diagram schematically illustrating an entire endoscope system including a multilayer board according to a first embodiment. An endoscope system 1 is a system that performs an ultrasound diagnosis inside a subject, such as a person, by using an ultrasound endoscope. The endoscope system 1 includes, as illustrated in FIG. 1, an ultrasound endoscope 2, an ultrasound imaging device 3, an endoscope imaging device 4, a display device and a light source device 6.

The ultrasound endoscope 2, at a distal end portion thereof, converts an electrical pulse signal received from the ultrasound imaging device 3 to an ultrasound pulse (acoustic pulse), applies the ultrasound pulse to the subject, converts an ultrasound echo reflected by the subject to an electrical echo signal that represents the ultrasound echo by a voltage change, and outputs the electrical echo signal.

The ultrasound endoscope 2 normally includes an imaging optical system and an image sensor, is inserted into a digestive tract (an esophagus, a stomach, a duodenum, or a large intestine) or a respiratory organ (a trachea or a bronchus) of the subject, and is able to capture an image of the digestive tract or the respiratory organ. Further, the ultrasound endoscope 2 is able to capture an image of a peripheral organ (a pancreas, a gallbladder, a bile duct, a biliary tract, lymph nodes, a mediastinal organ, a blood vessel, or the like) by using ultrasound waves. Furthermore, the ultrasound endoscope 2 includes a light guide that guides illumination light that is applied to the subject at the time of optical imaging. A distal end portion of the light guide is extended to a distal end of an insertion portion of the ultrasound endoscope 2 that is to be inserted into the subject, and a proximal end portion of the light guide is connected to the light source device 6 that generates the illumination light.

The ultrasound endoscope 2 includes, as illustrated in FIG. 1, an insertion portion 21, an operating unit 22, a universal cord 23, and a connector 24. The insertion portion 21 is a portion to be inserted into the subject. The insertion portion 21 includes, as illustrated in FIG. 1, a distal end rigid portion 211 that is arranged on a distal end side, that holds an ultrasound transducer 7 for transmitting and receiving ultrasound waves, and that has rigidity, a bendable portion 212 that is connected to a proximal end side of the distal end rigid portion 211 and that is bendable, and a flexible tube portion 213 that is connected to a proximal end side of the bendable portion 212 and that has flexibility. Here, in the insertion portion 21, a light guide for transmitting the illumination light supplied from the light source device 6 and a plurality of signal cables for transmitting various signals are routed, and a treatment tool insertion path for inserting a treatment tool is formed, although specific illustration is omitted. Meanwhile, in the present specification, one side of the insertion portion 21 at the side of the ultrasound transducer 7 is referred to as a distal end side, and another side connected to the operating unit 22 is referred to as a proximal end side.

Figure 2:
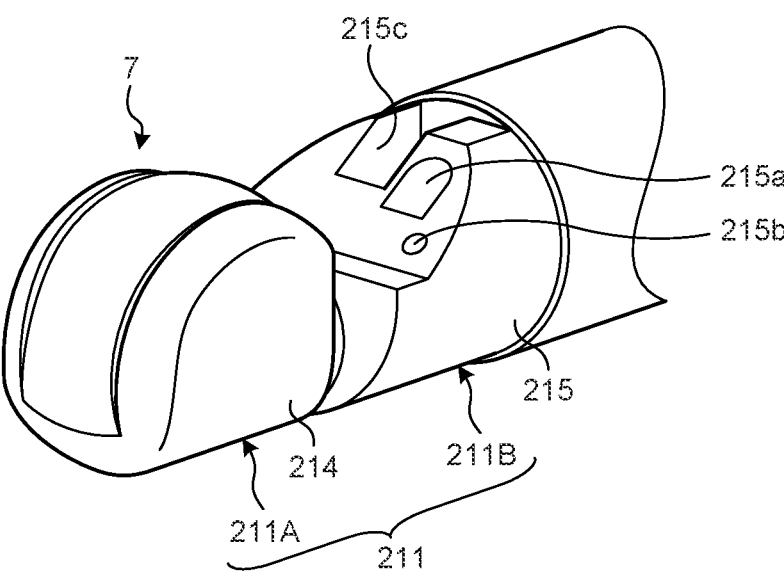
FIG. 2 is a perspective view schematically illustrating a configuration of a distal end of an insertion portion of an ultrasound endoscope illustrated in FIG. 1.
Figure 3:
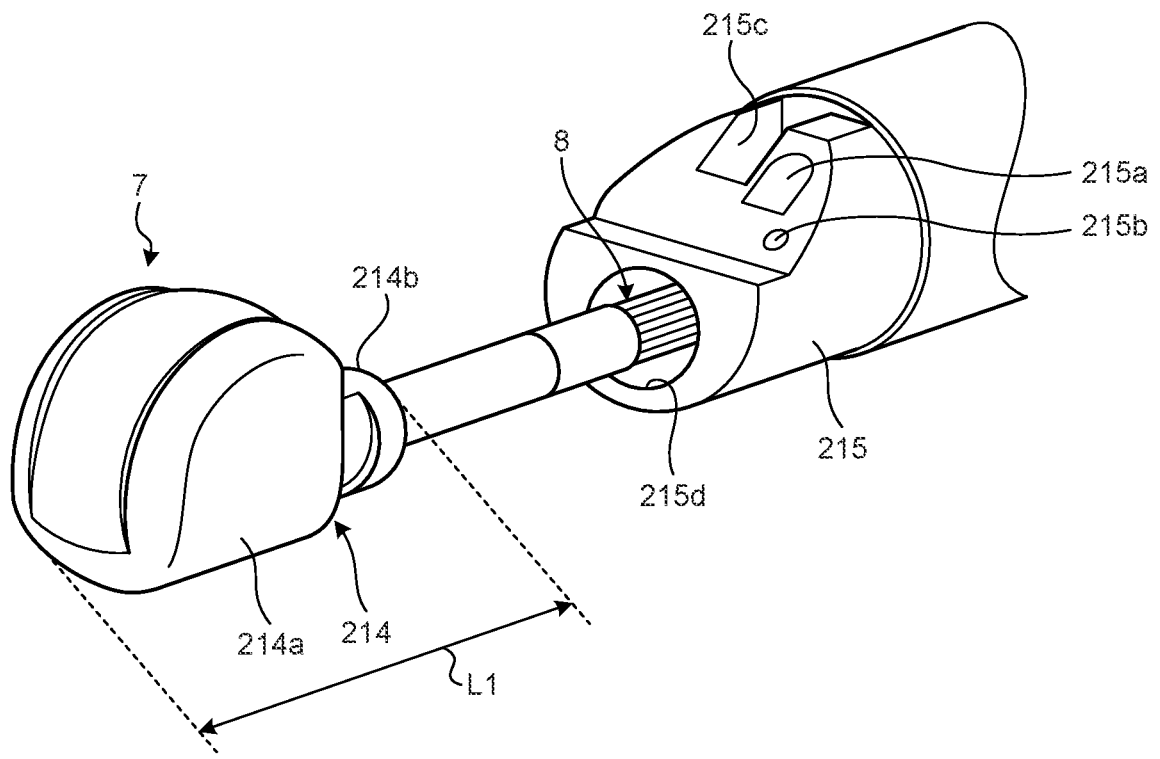
FIG. 3 is an exploded perspective view schematically illustrating the configuration of the distal end of the insertion portion of the ultrasound endoscope illustrated in FIG. 1.

FIG. 2 is a perspective view schematically illustrating a configuration of the distal end of the insertion portion of the ultrasound endoscope according to the present embodiment. FIG. 3 is an exploded perspective view schematically illustrating the configuration of the distal end of the insertion portion of the ultrasound endoscope according to the present embodiment. As illustrated in FIG. 2, the ultrasound transducer 7 is, for example, a convex transducer, but may be a radial transducer or a linear transducer. The ultrasound endoscope 2 includes, for example, 128 piezoelectric elements that are arranged in an array manner and that serve as the ultrasound transducer 7, and performs electronic scanning by electronically switching between the piezoelectric elements that perform transmission and reception or delaying transmission and reception of each of the piezoelectric elements. However, the number of the piezoelectric elements is not specifically limited.

The distal end rigid portion 211 includes an ultrasound function unit 211A in which the ultrasound transducer 7 is arranged, and an endoscope function unit 211B that is formed of a second casing 215 that includes an observation window 215a for inputting light to an imaging optical system that includes an objective lens for capturing external light and an illumination window 215b as a part of an illumination optical system that collects illumination light and outputs the illumination light to outside. A treatment tool protrusion port 215c, which communicates with the treatment tool insertion path formed inside the insertion portion 21 and allows a treatment tool to protrude from the distal end of the insertion portion 21, is formed in the second casing 215. One end of the endoscope function unit 211B is removably connected to the ultrasound function unit 211A, and the other end of the endoscope function unit 211B is connected to the bendable portion 212.

The ultrasound function unit 211A is made of insulating single resin, and is removably connected to the endoscope function unit 211B as described above. Specifically, the ultrasound function unit 211A includes the ultrasound transducer 7 and a first casing 214 for holding the ultrasound transducer 7. The first casing 214 includes a main body 214a for holding the ultrasound transducer 7 and a connection portion 214b that protrudes from the main body 214a and is connected to the endoscope function unit 211B. In the following, a length of the first casing 214 along a longitudinal direction will be referred to as a distal-end rigid length L1. The second casing 215 of the endoscope function unit 211B includes a hole portion 215d that is arranged, as a counterpart of the connection portion 214b, on an end portion of the endoscope function unit 211B at a side opposite to a side at which the bendable portion 212 is connected, and that is connected to the first casing 214. The ultrasound function unit 211A and the endoscope function unit 211B are connected to each other by fitting the connection portion 214b to the hole portion 215d. In this case, the ultrasound function unit 211A and the endoscope function unit 211B may be fixed to each other by a well-known method using an adhesive, a screw, or the like.

Referring back to FIG. 1, the operating unit 22 is a portion that is connected to a proximal end side of the insertion portion 21, and receives various kinds of operation from a doctor or the like. The operating unit 22 includes, as illustrated in FIG. 1, a bending knob 221 for performing bending operation on the bendable portion 212, and a plurality of operating members 222 for performing various kinds of operation. Furthermore, a treatment tool insertion port 223, which communicates with the treatment tool insertion path and allows a treatment tool to be inserted into the treatment tool insertion path, is formed in the operating unit 22.

The universal cord 23 is a cable which extends from the operating unit 22 and in which a plurality of signal cables for transmitting various signals, an optical fiber for transmitting illumination light supplied from the light source device 6, and the like are arranged.

The connector 24 is arranged on a distal end of the universal cord 23. Further, the connector 24 includes a first connector 241, a second connector 242, and a third connector 243 to which an ultrasound cable 31, a video cable 41, and an optical fiber cable 61 are connected, respectively.

The ultrasound imaging device 3 is electrically connected to the ultrasound endoscope 2 via the ultrasound cable 31 (see FIG. 1), outputs a pulse signal to the ultrasound endoscope 2 via the ultrasound cable 31, and inputs an echo signal from the ultrasound endoscope 2. Further, the ultrasound imaging device 3 performs predetermined processing on the echo signal and generates an ultrasound image.

The endoscope imaging device 4 is electrically connected to the ultrasound endoscope 2 via the video cable 41 (see FIG. 1), and inputs an image signal from the ultrasound endoscope 2 via the video cable 41. Further, the endoscope imaging device 4 performs predetermined processing on the image signal and generates an endoscopic image.

The display device 5 is configured with liquid crystal, organic electro luminescence (EL), a projector, a cathode ray tube (CRT), or the like, and displays an ultrasound image that is generated by the ultrasound imaging device 3, an endoscopic image that is generated by the endoscope imaging device 4, or the like.

The light source device 6 is connected to the ultrasound endoscope 2 via the optical fiber cable 61 (see FIG. 1), and supplies illumination light for illuminating the inside of the subject to the ultrasound endoscope 2 via the optical fiber cable 61.

Configuration of Cable Group

Figure 4:
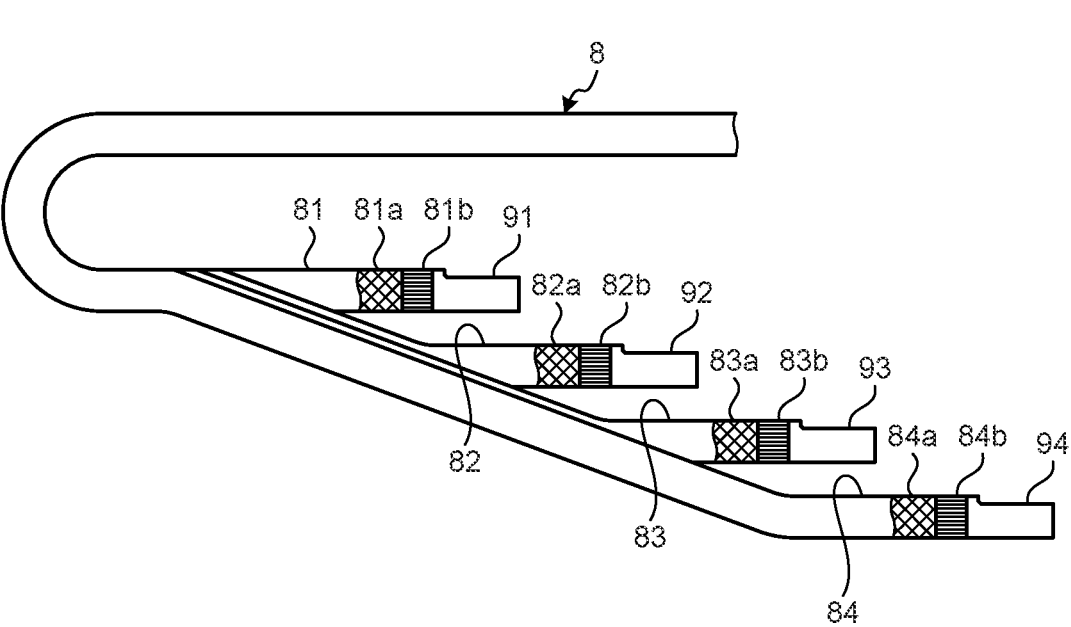
FIG. 4 is a diagram illustrating a state in which a cable group is connected to a flexible board.

A cable group 8 illustrated in FIG. 3 is connected to the ultrasound transducer 7 via a flexible board inside the first casing 214. FIG. 4 is a diagram illustrating a state in which the cable group is connected to the flexible board. As illustrated in FIG. 4, the cable group 8 is divided into four shield lines 81 to 84, for example. However, the number of the shield lines is not specifically limited. Furthermore, ground lines 81a to 84a and 32 signal lines 81b to 84b that are inserted in the ground lines 81a to 84a are connected to boards 91 to 94, respectively. A total number (128) of the signal lines 81b to 84b is the same as to the total number (128) of the piezoelectric elements of the ultrasound transducer 7, and a single signal line included in the plurality of signal lines 81h to 84b is connected to a single piezoelectric element of the ultrasound transducer 7 via any of the boards 91 to 94. However, the total number of the signal lines 81b to 84b is not specifically limited as long as the total number is the same as the total number of the piezoelectric elements.

Configuration of Flexible Board

Figure 5:
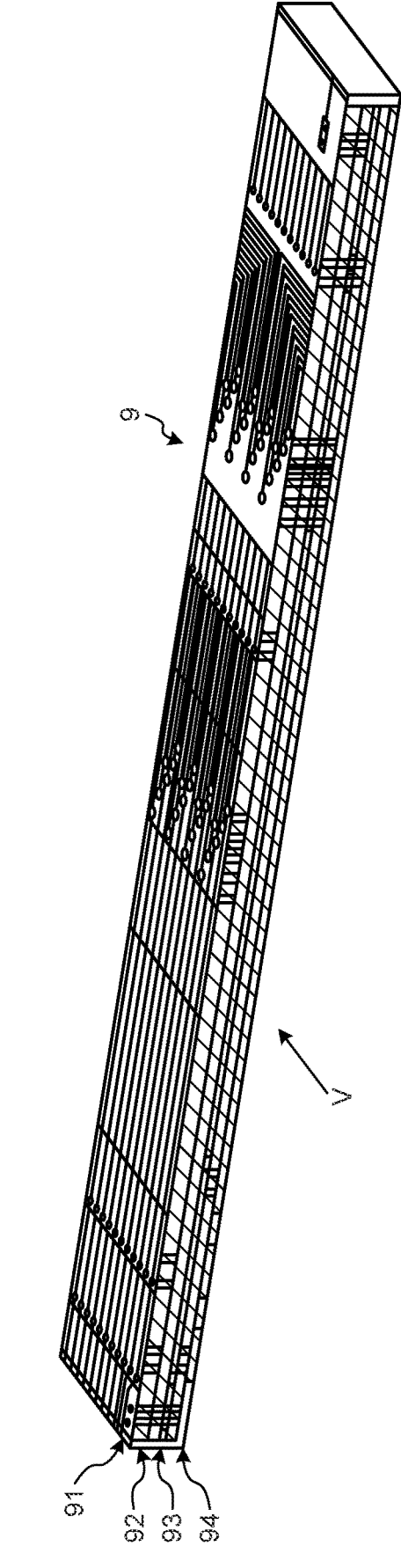
FIG. 5 is a perspective view of the flexible board.

FIG. 5 is a perspective view of the flexible board that is electrically connected to the piezoelectric elements of the ultrasound transducer 7 and the plurality of signal lines 81b to 84b. As illustrated in FIG. 5, a flexible board 9 is a flexible multilayer board in which boards are laminated along a lamination direction, and includes the boards 91 to 94. Specifically, the flexible board 9 as illustrated in FIG. 5 is formed by laminating the boards 91 to 94 illustrated in FIG. 4. However, the multilayer board need not always have flexibility. One end of the flexible board 9 (on a left side of the flexible board 9 in a longitudinal direction in FIG. 5) is connected to the shield lines 81 to 84 of the cable group 8, and the other end (on a right side of the flexible board 9 in the longitudinal direction in FIG. 5) is connected to the piezoelectric elements of the ultrasound transducer 7. In the following description, a side at the side of the board 91 will be referred to as a front side, and a side at the side of the board 94 will be referred to as a back side. In other words, the board 91 is a front-side layer, the board 92 and the board 93 are intermediate layers, and the board 94 is a back-side layer.

Figure 6:
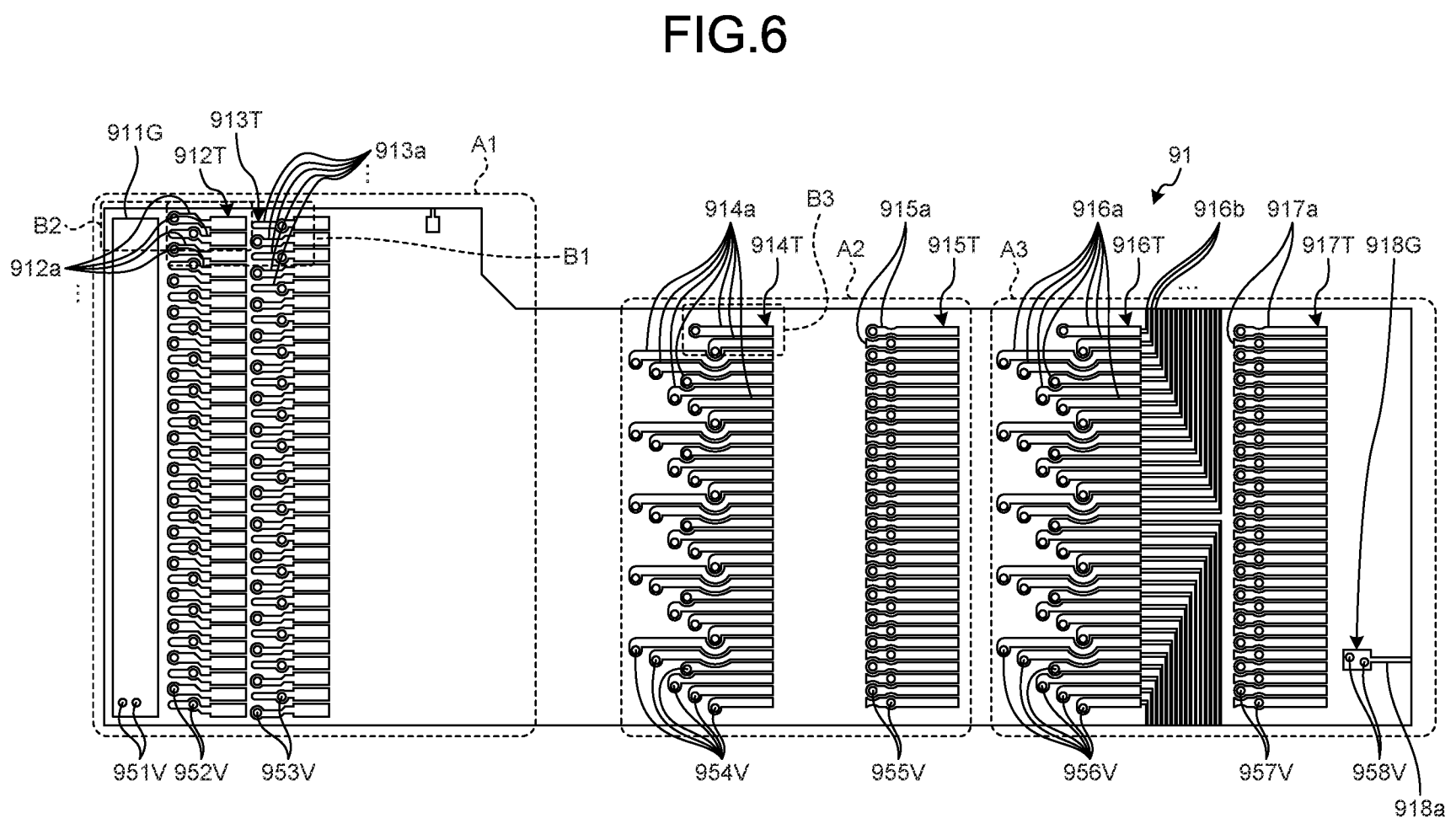
Figure 7:
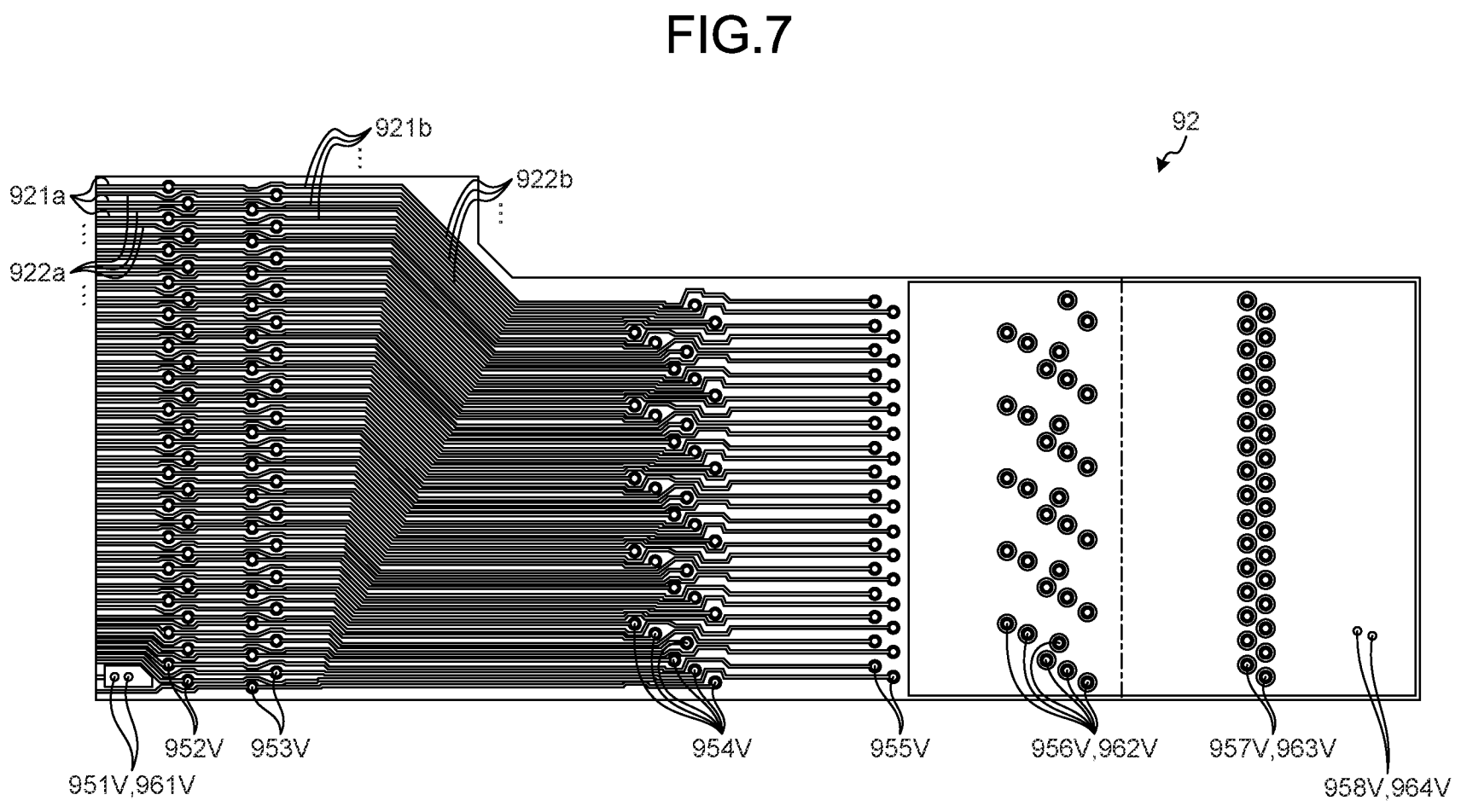
Figure 8:
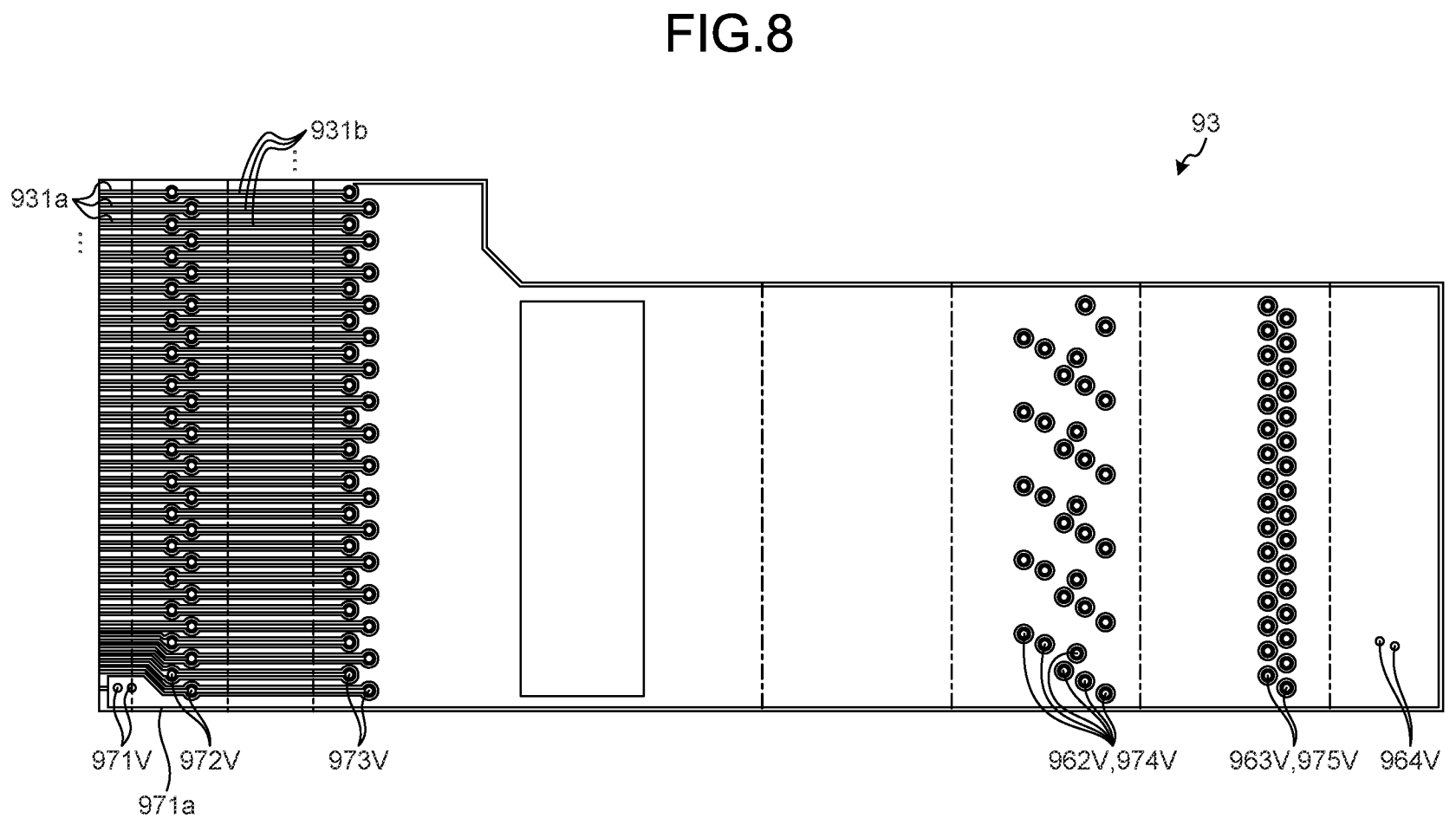
Figure 9:
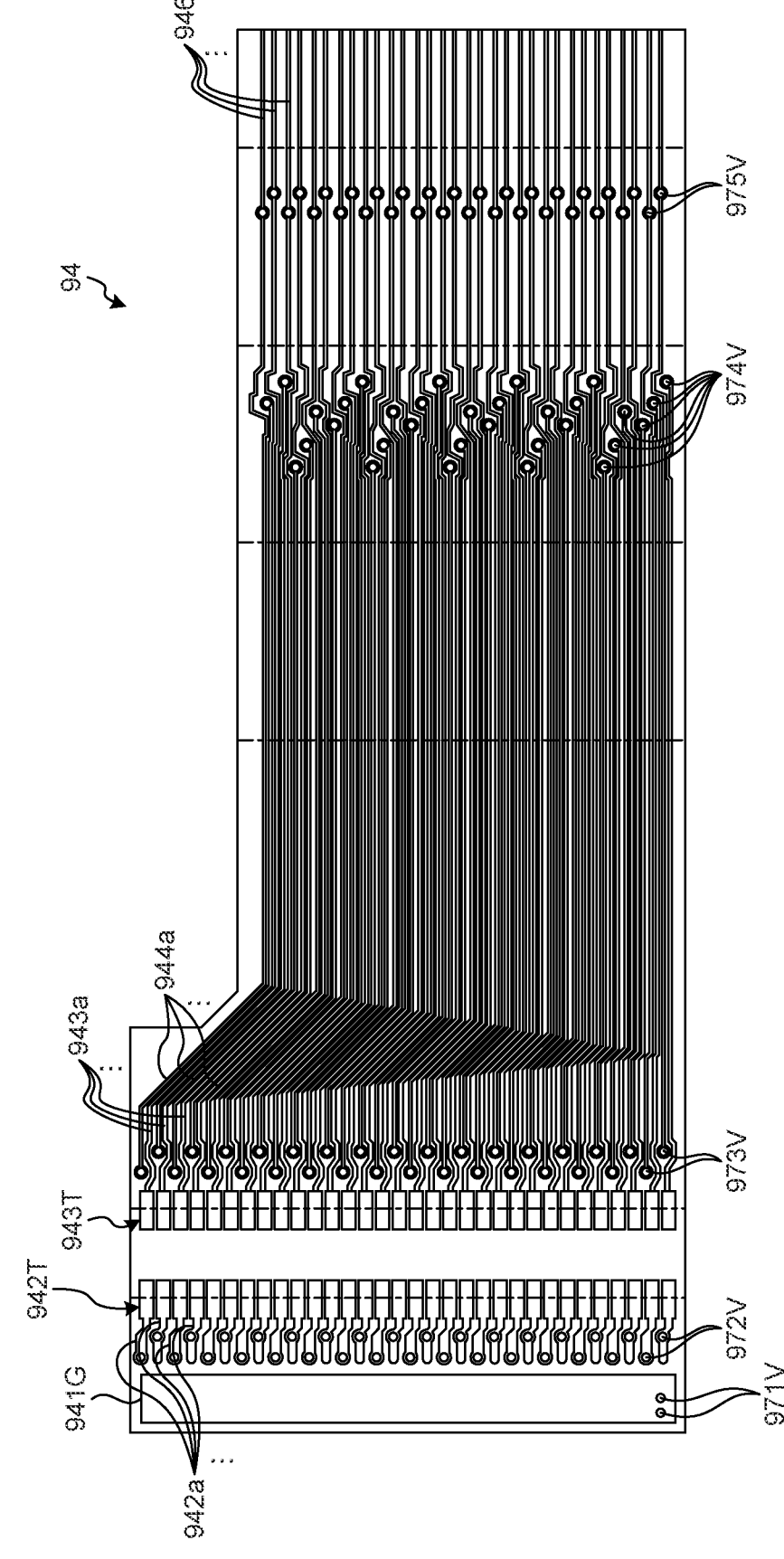
FIG. 9 is an enlarged view of a board.

FIG. 6 to FIG. 9 are enlarged views of the boards. FIG. 6 illustrates the board 91, FIG. 7 illustrates the board 92, FIG. 8 illustrates the board 93, and FIG. 9 illustrates the board 94. In the following description, the number of each of terminals and the number of wires will be described as examples, but the numbers are not specifically limited and may be changed depending on the number of the ultrasound transducers 7.

As illustrated in FIG. 6, on the board 91, a ground terminal 911G, 32 signal line connecting terminals 912T (signal line connecting terminal array), 32 signal line connecting terminals 913T (signal line connecting terminal array), 32 element connecting terminals 914T (element connecting terminal array), 32 element connecting terminals 915T (element connecting terminal array), 32 element connecting terminals 916T (element connecting terminal array), and 32 element connecting terminals 917T (element connecting terminal array), and a ground terminal 918G are formed. The ground terminal 911G is arranged in an end portion on one side (the left side in FIG. 6) in the longitudinal direction perpendicular to the lamination direction (a direction perpendicular to the sheet of FIG. 6), and connected to the ground lines 81a and 82a. The signal line connecting terminals 912T are arranged in the vicinity of the ground terminal 911G and connected to the respective 32 signal lines 82b. The signal line connecting terminals 913T are arranged adjacent to the signal line connecting terminals 912T and connected to the respective 32 signal lines 81b. The signal line connecting terminals 912T and the signal line connecting terminals 913T are arranged at deviated positions along the longitudinal direction of the flexible board 9. The element connecting terminals 914T to 917T are arranged in an end portion on the other side in the longitudinal direction (the right side in the longitudinal direction in FIG. 6) among directions perpendicular to the lamination direction, and electrically connected to the respective piezoelectric elements of the ultrasound transducer 7. The element connecting terminals 914T to 917T are arranged on the front-side layer side, and arranged at deviated positions along the longitudinal direction of the flexible board 9. The ground terminal 918G is arranged in the end portion on the other side in the longitudinal direction (the right side in the longitudinal direction in FIG. 6) among the directions perpendicular to the lamination direction, and connected to a ground line of the ultrasound transducer 7. Each of Vias 951V to 958V allows an electrical connection between each of the ground terminals 911G to 918G and the board 92. Wires 912a to 917a establish connections between the signal line connecting terminals 912T to the element connecting terminals 917T and the vias 952V to 957V. Wires 916b have thermal conductivity and are extended from the element connecting terminals 916T to an end of the board 91 in a vertical direction of the board 91. A wire 918a is connected to the ground line of the ultrasound transducer 7.

As illustrated in FIG. 7, wires 921a and 922a have thermal conductivity and are extended to an end of the board 92. Wires 921b are connected to the vias 952V and the vias 955V. Wires 922b are connected to the vias 953V and the vias 954V.

As illustrated in FIG. 8, vias 971V to 975V are electrically connected to the board 94 (see FIG. 9). Wires 931a have thermal conductivity and are extended from the vias 972V to an end of the board 93. Wires 931b are connected to the vias 972V and the vias 973V.

As illustrated in FIG. 9, on the board 94, a ground terminal 941G, 32 signal line connecting terminals 942T (signal line connecting terminal array), and 32 signal line connecting terminals 943T (signal line connecting terminal array) are formed. The ground terminal 941G is arranged in an end portion on one side in a longitudinal direction (the left side in the longitudinal direction in FIG. 9) among directions perpendicular to the lamination direction (the direction perpendicular to the sheet of FIG. 9), and connected to the ground lines 83a and 84a. The signal line connecting terminals 942T are arranged in the vicinity of the ground terminal 941G and connected to the respective 32 signal lines 83b. The signal line connecting terminals 943T are arranged adjacent to the signal line connecting terminals 942T and connected to the respective 32 signal lines 84b. Specifically, the signal line connecting terminals 942T and the signal line connecting terminals 943T are arranged at deviated positions along the longitudinal direction of the flexible board 9. The vias 971V allow electrical connections between the ground terminal 941G and the board 93. The vias 973V allow electrical connections between the signal line connecting terminals 942T and the board 93. The vias 973V allow an electrical connection between the board 94 and the board 93. The vias 974V allow an electrical connection between the board 94 and the board 91 via vias 962V and the vias 956V. The vias 975V allow the electrical, connection between the board 94 and the board 91 via vias 963V and the vias 957V. Wires 942a establish connections between the signal line connecting terminals 942T and the vias 972V. Wires 943a establish connections between the signal line connecting terminals 943T and the vias 974V. Wires 944a establish connections between the vias 973V and the vias 975V. Wires 946a have thermal conductivity and are extended from the vias 975V to an end of the board 94.

In FIG. 6 and FIG. 9 that illustrate plan views of the flexible board 9 along the lamination direction, it is preferable that both ends of each of the ground terminal 911G, the signal line connecting terminals 912T, the signal line connecting terminals 913T, the ground terminal 941G, the signal line connecting terminals 942T, and the signal line connecting terminals 943T in an arrangement direction (a vertical direction in FIG. 6 and FIG. 9) that crosses the longitudinal direction are located in a range of equal to or larger than 0.005 millimeter (mm) and equal to or smaller than 0.2 mm with respect to edges of the flexible board 9. This is to reduce a size of the flexible board 9 and reduce a size of the distal end of the insertion portion 21. To insert the ultrasound endoscope 2 into a body, it is very important to reduce the size of the distal end of the insertion portion 21 to reduce a burden on the body of a patient.

Figure 10:
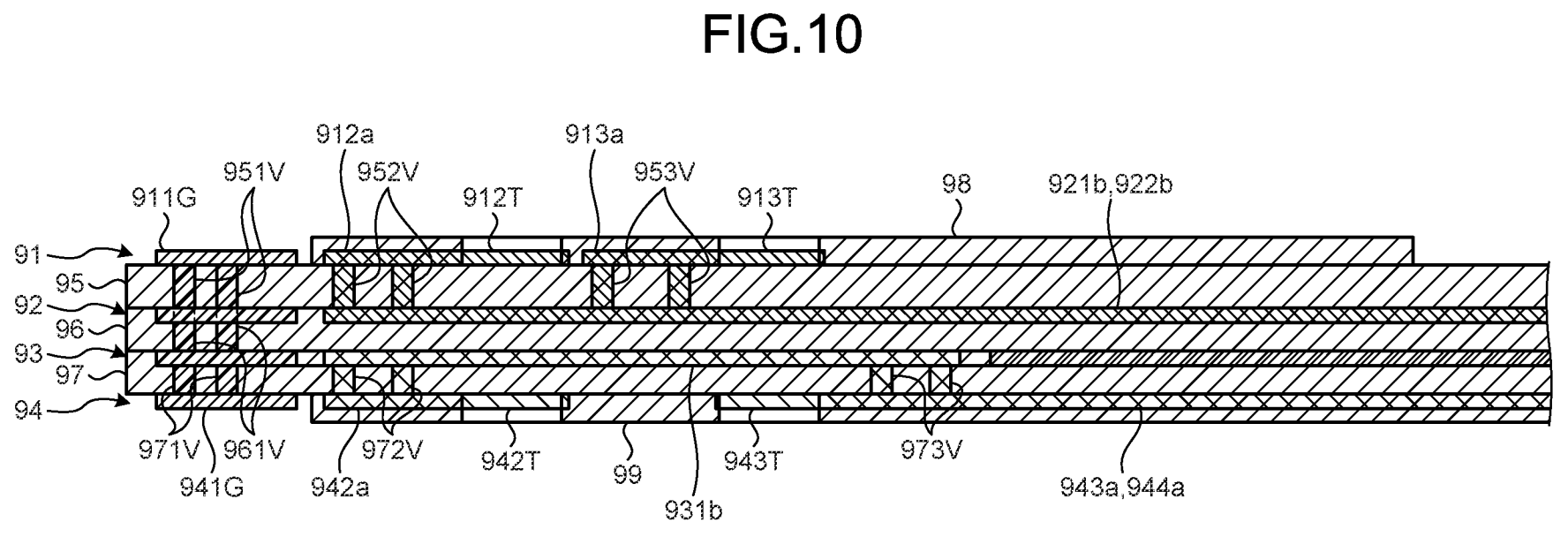
Figure 11:
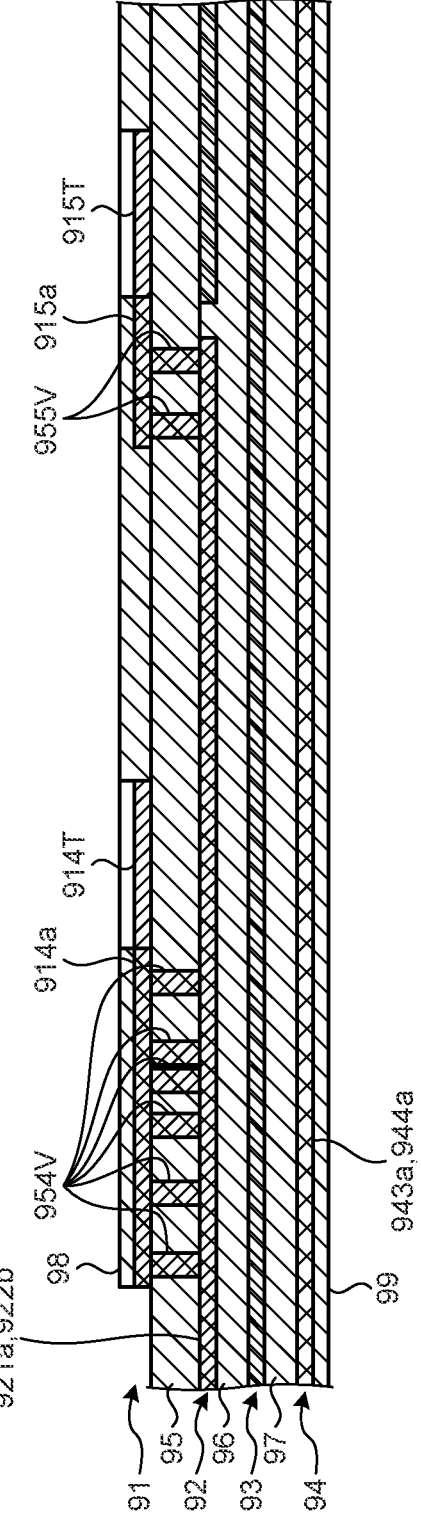
FIG. 11 is a partial projection view of the flexible board.
Figure 12:
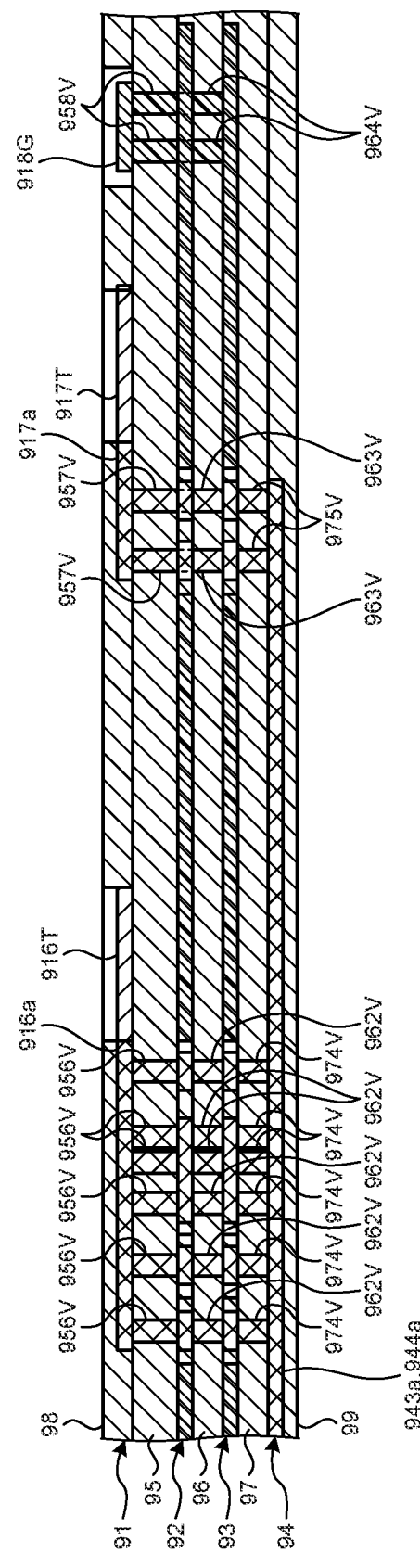
FIG. 12 is a partial projection view of the flexible board.

FIG. 10 to FIG. 12 are partial projection views of the flexible board. Specifically, FIG. 10 to FIG. 12 are projection views that illustrate the terminals, the wires, the vias, and the like that are projected in a direction along an arrow V in FIG. 5 when the flexible board 9 is viewed in a direction indicated by the arrow V (from below in FIG. 6 to FIG. 9). Therefore, in the drawings, some of the terminals, the wires, and the like overlap with one another, and integrally-illustrated portions and partially-illustrated portions are included. Furthermore, FIG. 10 is a view corresponding to a region A1 in FIG. 6, FIG. 11 is a view corresponding to a region A2 in FIG. 6, and FIG. 12 is a view corresponding to a region A3 in FIG. 6.

Polyimide base materials 95 to 97 are arranged, as insulating layers, between the boards 91 to 94. The polyimide base materials 95 to 97 include vias as thermal conduction portions that have thermal conductivity and that are arranged between each of the board 91 as the front-side layer and the board 94 as the back-side layer and the boards 92 and 93 as the intermediate layers.

Furthermore, a front side of the board 91 and a back side of the board 94 are covered by resists 98 and 99. The resists 98 and 99 expose only each of terminal portions and protect the other portions on the front side of the board 91 and the back side of the board 94.

As illustrated in FIG. 10, the ground terminal 911G and the ground terminal 941G face each other in the lamination direction and constitute a part of the board 91 and the board 94. Further, each of the signal line connecting terminals 912T and the signal line connecting terminals 913T faces each of the signal line connecting terminals 942T and the signal line connecting terminals 943 in the lamination direction, and the signal line connecting terminals constitute a part of the board 91 the board 94.

The ground terminal 911G and the ground terminal 941G are connected to each other via the vias 951V, vias 961V, and the vias 971V, and have the same potentials. In other words, the flexible board 9 includes the vias 951V, 961V, and 971V that are located in the vicinity of the end portion of the flexible board 9 in the longitudinal direction and that electrically connect the ground terminal. 911G of the front-side layer and the ground terminal 941G of the back-side layer. Further, the vias 951V, 961V, and 971V are arranged at positions overlapping with the ground terminal 911G and the ground terminal 941G in the lamination direction. Furthermore, the vias 971V and the vias 964V are connected to each other via an electrode 971a as illustrated in FIG. 8, and the vies 964V are connected to the ground terminal 918G via the vias 958V as illustrated in FIG. 12, so that the ground terminal 918G has the same potential as the ground terminal 911G and the ground terminal 941G.

As illustrated in FIG. 10 to FIG. 12, the signal line connecting terminals 912T are connected to the element connecting terminals 915T via the wires 912a, the vias 952V, the wires 921b, the vias 955V, and the wires 915a.

The signal line connecting terminals 913T are connected to the element connecting terminals 914T via the wires 913a, the vies 953V, the wires 922b, the vies 954V, and the wires 914a.

The signal line connecting terminals 942T are connected to the element connecting terminals 917T via the wires 942a, the vias 972V, the wire 931b, the vias 973V, the wire 944a, the vias 975V, the vias 963V, the vias 957V, and the wires 917a.

The signal line connecting terminals 943T are connected to the element connecting terminals 916T via the wires 943a, the vies 974V, the vias 962V, the vies 956V, and the wires 916a.

Figure 13A:
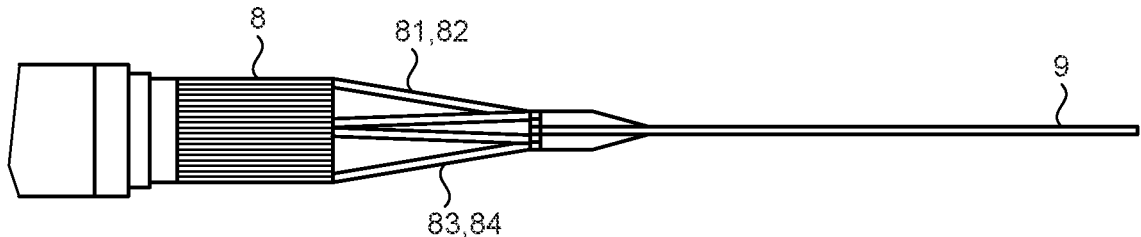
FIGS. 13A and 13B are enlarged views of a connection portion between the cable group and the flexible board.
Figure 13B:
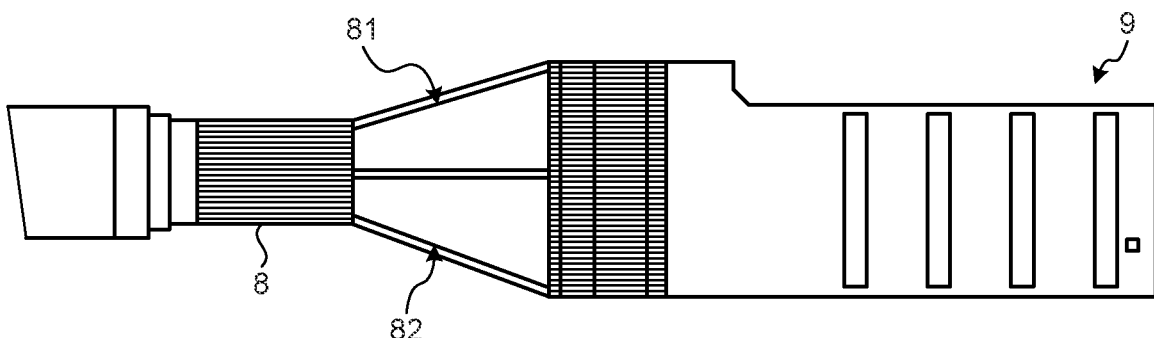

FIGS. 13A and 13B are enlarged views of a connection portion between the cable group and the flexible board. As illustrated in FIGS. 13A and 13B, the shield lines 81 to 84 of the cable group 8 are connected to front sides and back sides of the signal line connecting terminals 912T, 913T, 942T, and 943T of the flexible board 9.

Figure 14:
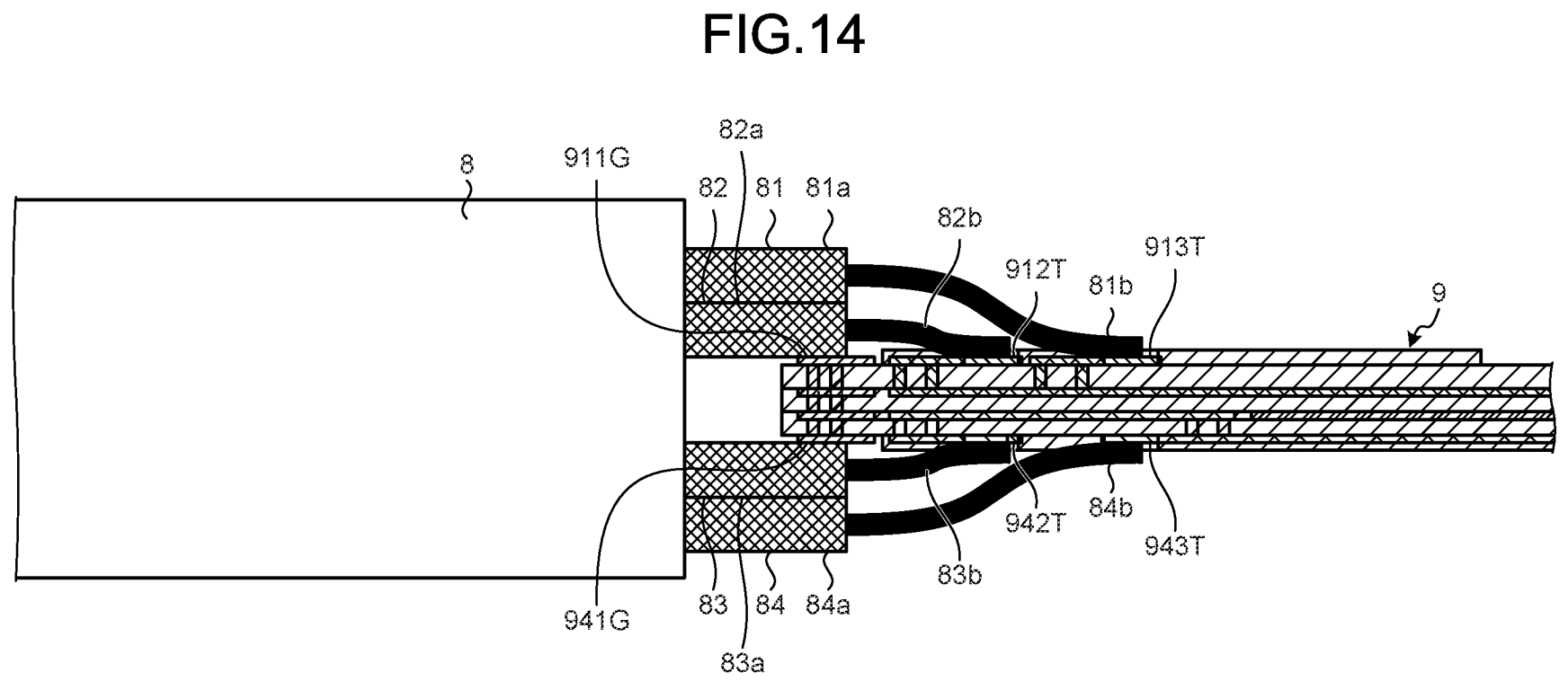

FIG. 14 is an enlarged view of the connection portion between the cable group and the flexible board. As illustrated in FIG. 14, on the front side of the flexible board 9, the ground lines 81a and 82a are connected to the ground terminal 911G of the board 91, the signal lines 82b are connected to the signal line connecting terminals 912T, and the signal lines 81b are connected to the signal line connecting terminals 913T. Similarly, on the back side of the flexible board 9, the ground lines 83a and 84a are connected to the ground terminal 941G of the board 94, the signal lines 83b are connected to the signal line connecting terminals 942T, and the signal lines 84b are connected to the signal line connecting terminals 943T.

Figure 15:
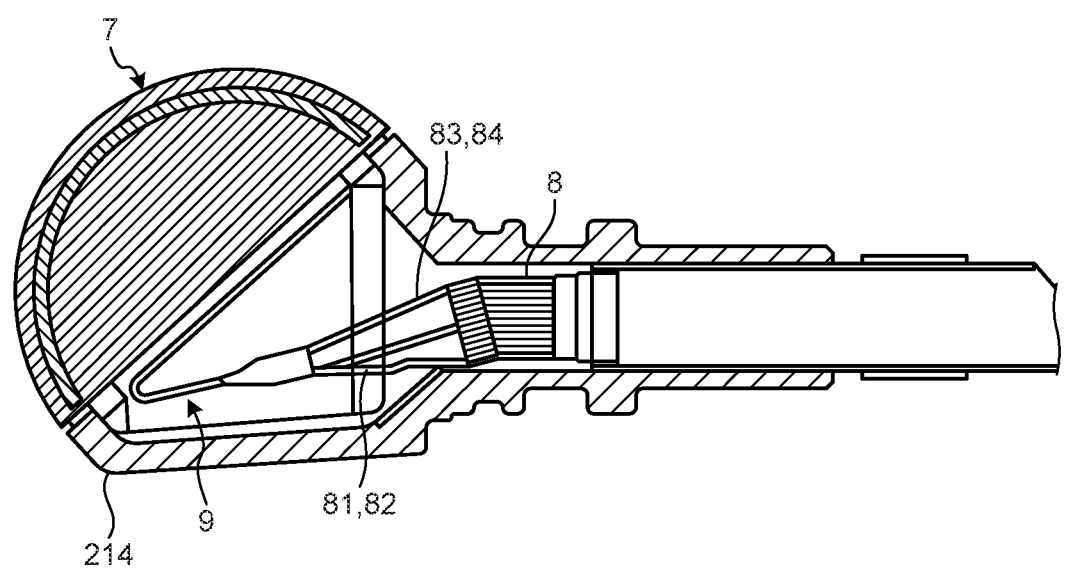
FIG. 15 is a cut-out view illustrating an internal configuration of a distal end portion of the ultrasound endoscope.

FIG. 15 is a cut-out view illustrating an internal configuration of a distal end portion of an ultrasound endoscope. As illustrated in FIG. 15, the cable group 8 and the flexible board 9 that are connected to each other are connected to the piezoelectric elements of the ultrasound transducer 7 and housed in the first casing 214. In this case, it is possible to reduce the distal-end rigid length L1 by housing the flexible board 9 in a bending manner in the first casing 214.

As described above, the signal line connecting terminals 912T, the signal line connecting terminals 913T, the signal line connecting terminals 942T, and the signal line connecting terminals 943T of the flexible board 9 are respectively connected to the element connecting terminals 915T, the element connecting terminals 914T, the element connecting terminal 917T, and the element connecting terminals 916T in this order, and connect the 128 signal lines of the cable group 8 and the 128 piezoelectric elements of the ultrasound transducer 7. According to the flexible board 9 as described above, it is possible to connect the cable group 8 so as to face the both sides of the flexible board 9, so that it is possible to reduce the distal-end rigid length L1.

Furthermore, in the flexible board 9, one of a set of the signal lines 81b and 82b and a set of the signal lines 83b and 84b is soldered to one of a set of the signal line connecting terminals 912T and 913T of the board 91 and a set of the signal line connecting terminals 942T and 943T of the board 94, and thereafter the flexible board 9 is inverted and the other set is soldered. If soldering on the board 91 is performed after soldering on the board 94 is performed, because the flexible board 9 is formed of the four layers of the boards 91 to 94, the boards 92 and 93 that are the intermediate layers reduce heat transmitted from the board 91 to the board 94 and the wires 921a, 922a, 931a, 916a, and 946a, dissipate heat from end faces when the signal lines 81b and 82b are soldered to the signal line connecting terminals 912T and 913T of the board 91; therefore, it is possible to prevent solder on the board 94 that has been subjected to soldering first from being melted again. Similarly, if soldering on the board 94 is performed after soldering on the hoard 91 is performed, the boards 92 and 93 block heat and the wires 921a, 922a, 931a, 916a, and 946a dissipate heat from end faces, so that it is possible to prevent solder on the board 91 from being melted again.

Figure 16:
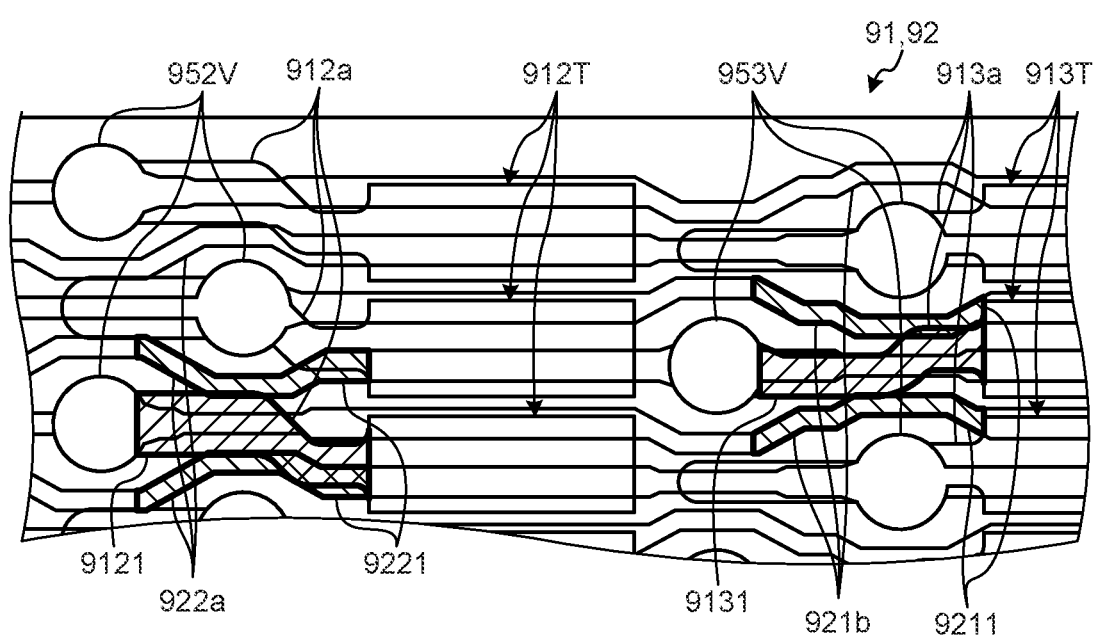
FIG. 16 is a diagram illustrating a state of wires on a first board and a second board.

FIG. 16 is a diagram illustrating a state of the wires on the first board and the second board. FIG. 16 is an enlarged view of a portion B1 in FIG. 6, in which the wires of the board 91 and the wires of the board 92 overlap with one another. In FIG. 16, a portion 9121 that is a part of the wires 912a and a portion 9221 that is a part of the wires 922a, which are emphasized by hatching, are arranged such that an overlapping area is reduced as much as possible. In this manner, a wiring pattern of the wires 922a of the board 92 as the intermediate layer is different from a wiring pattern of the wires 912a arranged on the board 91 as the front-side layer in a plane viewed along the lamination direction (a direction perpendicular to the sheet of FIG. 16). As a result, it is possible to increase a distance between the wires 912a and the wire 922a as compared to a case in which the wiring patterns are the same in a plane viewed along the lamination direction, so that it is possible to reduce heat that is transmitted from the wires 912a to the wire 922a at the time of soldering.

Similarly, a portion 9131 that is a part of the wires 913a and a portion 9211 that is a part of the wires 921b, which are emphasized by hatching, are arranged such that an overlapping area is reduced as much as possible. In this manner, a wiring pattern of the wires 921b of the board 92 as the intermediate layer is different from a wiring pattern of the wires 913a arranged on the board 91 as the front-side layer in a plane viewed along the lamination direction. As a result, it is possible to reduce neat that is transmitted from the wires 913a to the wires 921b at the time of soldering.

In FIG. 16, it is explained that, in the portion B1, the wiring pattern of the wires of the board 92 as the intermediate layer is different from the wiring pattern of the wires arranged on the board 91 of the front-side layer in a plane viewed along the lamination direction; however, it is preferable that, in the entire region of the flexible board 9, the wiring pattern of the wires of the board 92 as the intermediate layer is different from the wiring pattern of the wires arranged on the board 91 of the front-side layer in a plane viewed along the lamination direction. Furthermore, it is preferable that the wiring pattern of the wires of the board 93 as the intermediate layer is different from the wiring pattern of the wires of the board 94 as the back-side layer in a plane viewed along the lamination direction. As a result, in the entire region of the flexible board 9, it is possible to reduce heat that is transmitted from the wires of the board 91 or the board 94 to the wires of the board 92 or the board 93 when soldering is performed.

Figure 17:
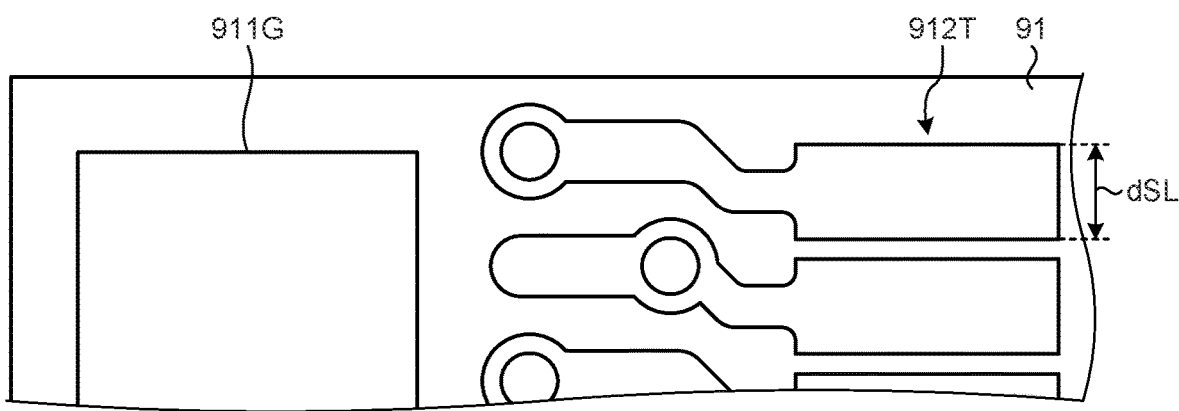
FIG. 17 is a partially enlarged view of the first board.
Figure 18:
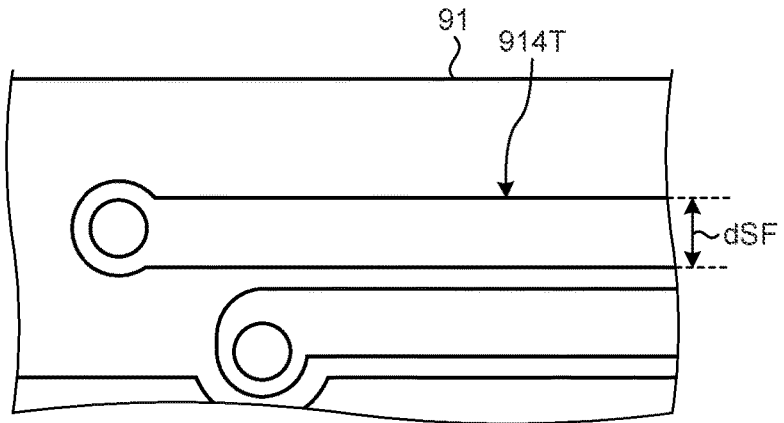
FIG. 18 is a partially enlarged view of the first board.

FIG. 17 and FIG. 18 are partially enlarged views of the first board. Specifically, FIG. 17 is a partially enlarged view of a portion B2 in FIG. 6, and FIG. 18 is a partially enlarged view of a portion B3 in FIG. 6. A width dSF of each of the signal line connecting terminals 912T in an arrangement direction in FIG. 17 is larger than a width dSF of each of the element connecting terminals 914T in the arrangement direction in FIG. 18. In this manner, in the flexible board 9, the widths of the signal line connecting terminals 912T, 913T, 942T, and 943T are larger than the widths of the element connecting terminals 914T to 917T in the arrangement direction. Further, in the flexible board 9, in the arrangement direction, widths between the signal line connecting terminals 912T, 913T, 942T, and 943T and widths between the element connecting terminals 914T to 917T are smaller than widths of each of wires arranged on the front-side layer and the back-side layer. As a result, it is possible to reduce the width of the flexible board 9 on the distal end side (at the side of the ultrasound transducer 7), so that it is possible to reduce the size of the insertion portion 21.

Second Embodiment

Figure 19:
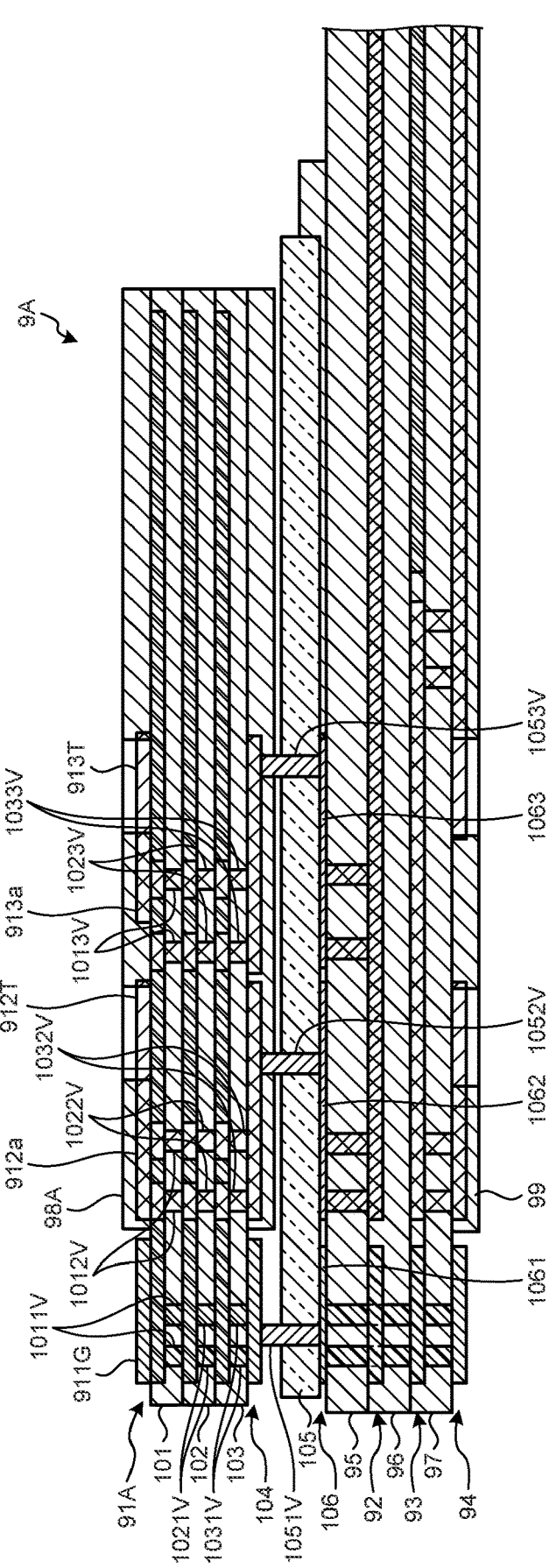
FIG. 19 is a partial cross-sectional view of a multilayer board according to a second embodiment.

FIG. 19 as a partial cross-sectional view of a multilayer board according to a second embodiment. As illustrated in FIG. 19, a flexible board 9A includes a board 91A, polyimide base materials 101 to 103, a relay board 104, a heat insulating layer 105 with high heat insulating property, and a relay board 106. The board 92, the board 93, the board 94, the polyimide base materials 95 to 97, and the resist 99 are the same as those of the first embodiment, and therefore, explanation thereof will be omitted.

The ground terminal 911G, the signal line connecting terminals 912T, and the signal line connecting terminals 913T are formed on the board 91A. A front side of the board 91A is protected by a resist 98A.

The ground terminal 911G has the same potential as the ground terminal 941G through the same route as in the first embodiment via vias 1011V of the polyimide base material 101, vias 1021V of the polyimide base material 102, vias 1031V of the polyimide base material 103, a via 1051V of the heat insulating layer 105, and a relay terminal 1061 of the relay board 106.

The signal line connecting terminals 912T are connected to the element connecting terminals 915T through the same route as in the first embodiment via the wires 912*a*, vias 1012V of the polyimide base material 101, vias 1022V of the polyimide base material 102, vias 1032V of the polyimide base material 103, a via 1052V of the heat insulating layer 105, and a relay terminal 1062 of the relay board 106.

The signal line connecting terminals 913T are connected to the element connecting terminals 914T through the same route as in the first embodiment via the wires 913*a*, vias 1013V of the polyimide base material 101, vias 1023V of the polyimide base material 102, vias 1033V of the polyimide base material 103, a via 1053V of the heat insulating layer 105, and a relay terminal 1063 of the relay board 106.

As described above, in the flexible board 9A, the heat insulating layer 105 with high heat insulating property is arranged between the board 91A and the board 94, so that it is possible to effectively reduce heat that is transmitted from the board 91A to the board 94. Furthermore, if the heat insulating layer 105 is an anisotropic conductive adhesive, insulating property in a layer direction is maintained while maintaining conductive property in the lamination direction, so that it is possible to further improve the effect of reducing heat that is transmitted from the board 91A to the board 94.

Third Embodiment

Figure 20:
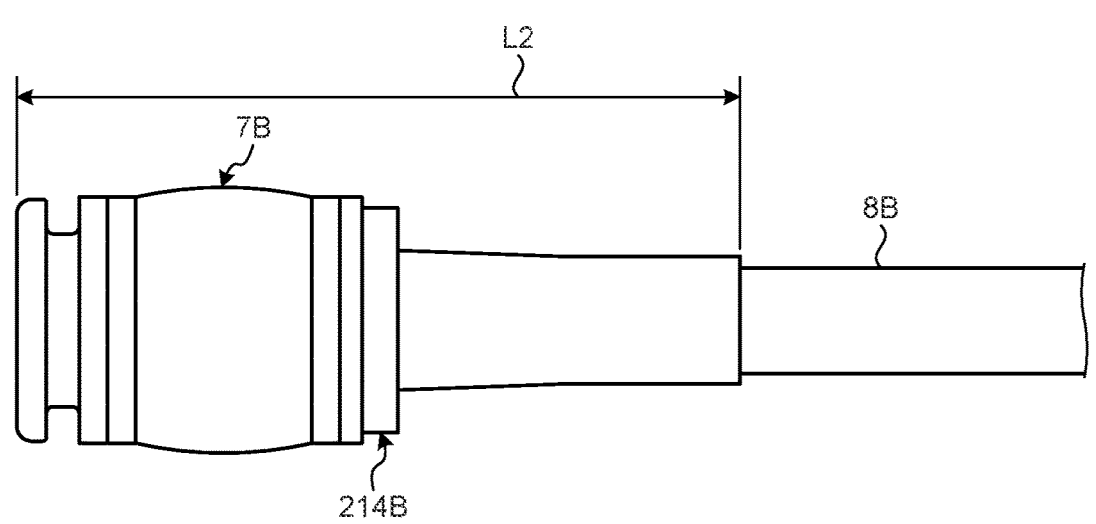
FIG. 20 is a side view of a distal end portion of an ultrasound endoscope.

FIG. 20 is a side view of a distal end portion of an ultrasound endoscope. As illustrated in FIG. 20, in a third embodiment, an ultrasound transducer 7B is a radial transducer and is held by a first casing 214B. If the ultrasound transducer 7B is a radial transducer, a distal-end rigid length 12 is the same as a length of the first casing 214B.

Figure 21:
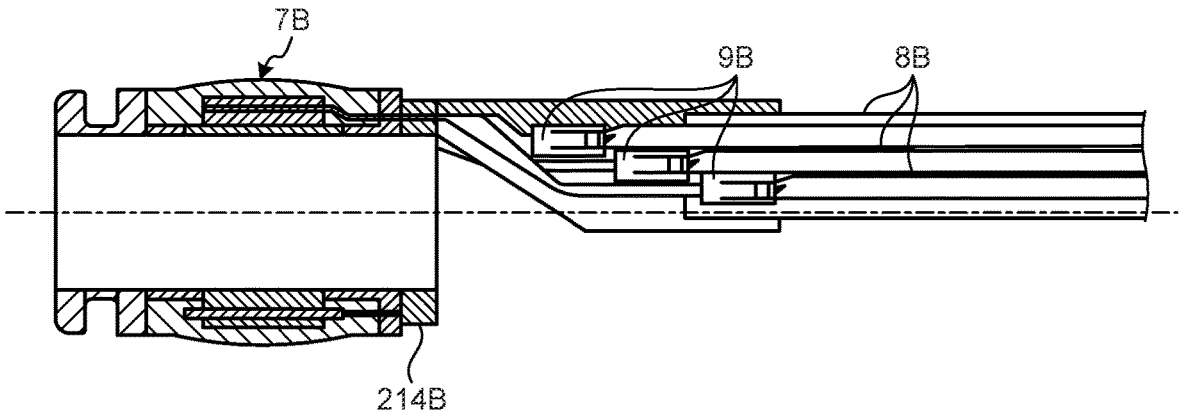
FIG. 21 is a cut-out view illustrating an internal configuration of a distal end portion of an ultrasound endoscope.

FIG. 21 is a cut-out view illustrating an internal configuration of the distal end portion of the ultrasound endoscope. As illustrated in FIG. 21, three flexible boards 9B are connected to the ultrasound transducer 7B, and three cable groups 8B are connected to the flexible boards 9B. In this manner, the plurality of boards need not be laminated.

Fourth Embodiment

Figure 22:
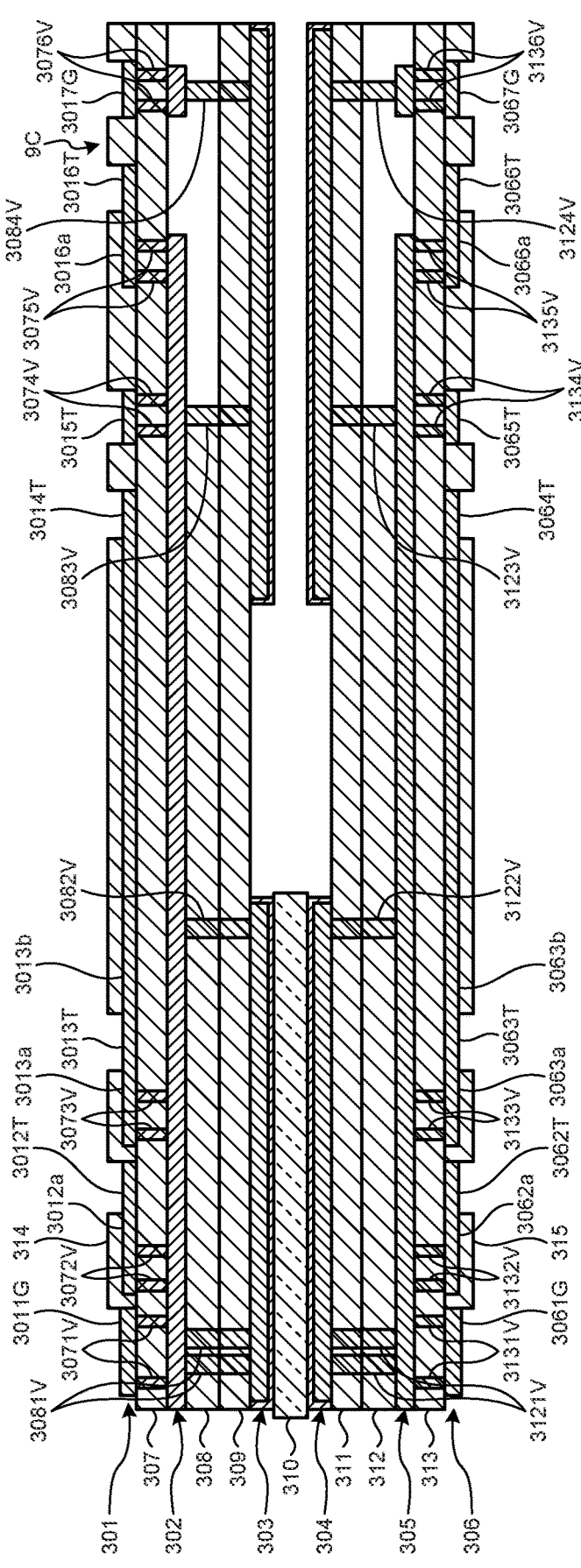
FIG. 22 a cross-sectional view of a multilayer board according to a fourth embodiment.

FIG. 22 is a cross-sectional view of a multilayer board according to a fourth embodiment. As illustrated in FIG. 22, a flexible board 9C includes boards 301 to 306, polyimide base materials 307, 308, 312, and 313 that are arranged between the boards 301 to 306, a bonding layer 309 that bonds the polyimide base material 308 and the board 303, a bonding layer 311 that bonds the polyimide base material 312 and the board 304, and a heat insulating layer 310. A front side of the board 301 and a back side of the board 306 are covered by resists 314 and 315, respectively.

A ground terminal 3011G of the board 301 and a ground terminal 3061G of the board 306 are arranged so as to face each other in the lamination direction. Further, a signal line connecting terminal 3012T and a signal line connecting terminal 3013T of the board 301 are arranged so as to respectively face a signal line connecting terminal 3062T and a signal line connecting terminal 3063T of the board 306. Furthermore, element connecting terminals 3014T to 3016T of the board 301 are arranged so as to face element connecting terminals 3064T to 3066T of the board 306. Moreover, a ground terminal 3017G of the board 301 and a ground terminal 3067G of the board 306 are arranged so as to face each other.

The ground terminal 3011G is connected to and has the same potential as the ground terminal 3017G via vias 3071V, vias 3081V, a wire of the board 303, a via 3082V, a wire of the board 302, a via 3083V, a wire of the board 303, a via 3064V, and vias 3076V. Similarly, the ground terminal 3061G is connected to and has the same potential as the ground terminal 3067G via vias 3131V, vias 3121V, a wire of the board 304, a via 3122V, a wire of the board 305, a via 3123V, a wire of the board 304, a via 3124V, and vias 3136V.

The signal line connecting terminal 3012T is connected to the element connecting terminal 30161 via a wire 3012*a*, vias 3072V, a wire of the board 302, vies 3075V, and a wire 3016*a*.

The signal line connecting terminal 3013T is connected to the element connecting terminal 30151 wire 3013*a*, vias 3073V, a wire of the board 302, and vias 3074V. Further, the signal line connecting terminal 3013T is connected to the element connecting terminal 3014T via a wire 3013*b*.

The signal line connecting terminal 3062T is connected to the element connecting terminal 3066T wire 3062*a*, vias 3132V, a wire of the board 305, vias 3135V, and a wire 3066*a*.

The signal line connecting terminal 3063T is connected to the element connecting terminal 3065T via a wire 3063*a*, vias 3133V, a wire of the board 305, and vias 3134V. Further, the signal line connecting terminal 3063T is connected to the element connecting terminal 3064T via a wire 3063*b*.

Figure 23:
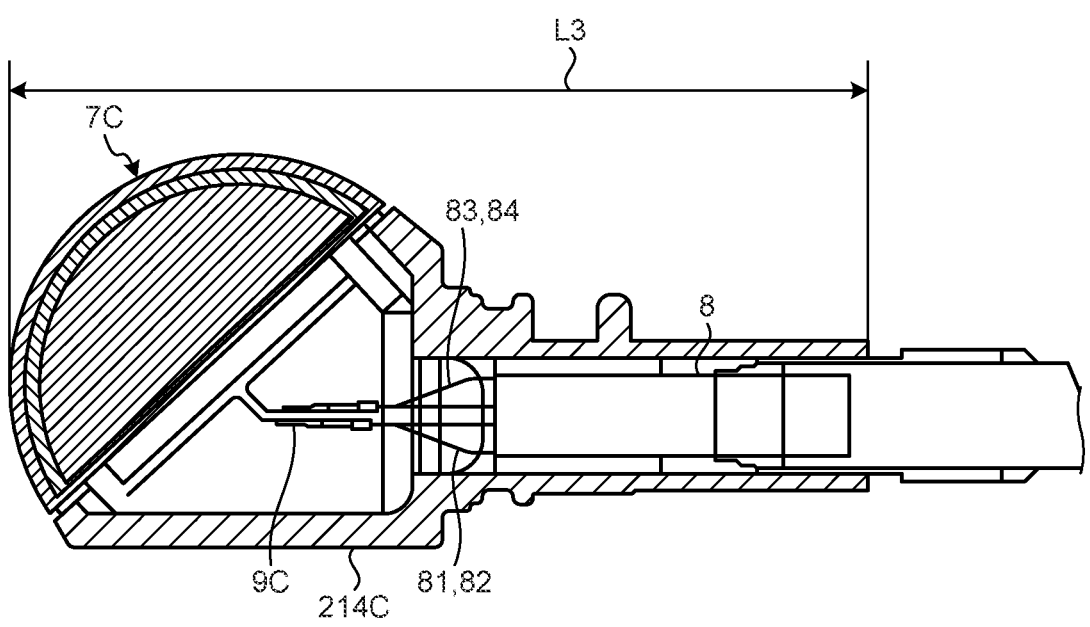
FIG. 23 is a cut-out view illustrating an internal configuration of a distal end portion of an ultrasound endoscope.

FIG. 23 is a cut-out view illustrating an internal configuration of the distal end portion of the ultrasound endoscope. As illustrated in FIG. 23, a distal end side of the flexible board 9C bends in two directions facing each other at an approximately right angle, is connected to a convex ultrasound transducer 7C, and is housed in a first casing 214C.

As described above, in the flexible board. 9C, the heat insulating layer 310 with high heat insulating property is arranged between the board 301 and the board 306, so that it is possible to effectively reduce heat that is transmitted from the board 301 to the board 306. Furthermore, it is possible to connect the ultrasound transducer 7C on both sides of the flexible board 9C whose distal end bends in two directions, so that it is possible to reduce a length, that is, a distal-end rigid length L3, of the first casing 214C.

According to the disclosure, it is possible to realize a multilayer board, a probe unit, and an ultrasound endoscope with a short distal-end rigid length.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multilayer board comprising:
a front-side layer;
an intermediate layer;
a back-side layer;
the front-side layer, the intermediate layer, and the back-side layer being laminated in a lamination direction of the multilayer board;
the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board;
a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively;

a plurality of signal line connecting terminal arrays each including a plurality of signal line connecting terminals for connecting respective signal lines of the shield lines, the plurality of signal line connecting terminal arrays forming a part of the front-side layer and a part of the back-side layer in a vicinity of the ground terminal in the longitudinal direction, the plurality of signal line connecting terminal arrays being arranged along the longitudinal direction; and
a wire having a thermal conductivity, the wire extending to the second end on the intermediate layer.

2. The multilayer board according to claim 1, wherein the wire has a different wiring pattern from wiring patterns of wires in a plane viewed along the lamination direction, the wires being arranged on the front-side layer and the back-side layer.

3. The multilayer board according to claim 1, further comprising:
a thermal conduction portion having a thermal conductivity, the thermal conduction portion being arranged between each of the front-side layer and the back-side layer and the intermediate layer.

4. The multilayer board according to claim 1, wherein when the multilayer board is viewed in a plane along the lamination direction, both ends of each of the ground terminal and the signal line connecting terminal arrays are located in a range of equal to or larger than 0.005 millimeter to equal to or smaller than 0.2 millimeter with respect to edges of the multilayer board.

5. The multilayer board according to claim 1, further comprising:
a via that is located in a vicinity of an end portion of the multilayer board in the longitudinal direction, the via being configured to electrically connect the first ground terminal of the front-side layer and the second ground terminal of the back-side layer.

6. The multilayer board according to claim 5, wherein the via is arranged at a position overlapping with the first ground terminals and the second ground terminal along the lamination direction.

7. The multilayer board according to claim 1, further comprising:
a plurality of element connecting terminal arrays each including a plurality of element connecting terminals for connecting respective piezoelectric elements included in the ultrasound transducer, the plurality of element connecting terminal arrays being arranged on the side of the first end of the multilayer board and being arranged along the longitudinal direction.

8. The multilayer board according to claim 7, wherein a width of each of the signal line connecting terminals is larger than a width of each of the element connecting terminals in an arrangement direction of the signal line connecting terminals.

9. The multilayer board according to claim 7, wherein a width of each of the signal line connecting terminal arrays is larger than a width of each of the element connecting terminal arrays in an arrangement direction of the signal line connecting terminals.

10. The multilayer board according to claim 7, wherein a width between the signal line connecting terminals and a width between the element connecting terminals are smaller than a width of each of wires arranged on the front-side layer and the back-side layer.

11. The multilayer board according to claim 7, wherein the element connecting terminal arrays form a part of the front-side layer or a part of the back-side layer.

US 12,569,883 B2

15

12. A probe unit comprising
a plurality of shield lines, and
a multilayer board comprising:
  a front-side layer;
  an intermediate layer;
  a back-side layer;
  the front-side layer, the intermediate layer, and the back-side layer being laminated in a lamination direction of the multilayer board;
  the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board;
a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively;
  a plurality of signal line connecting terminal arrays each including a plurality of signal line connecting terminals for connecting respective signal lines of the shield lines, the plurality of signal line connecting terminal arrays forming a part of the front-side layer and a part of the back-side layer is a vicinity of the ground terminal in the longitudinal direction, the plurality of signal line connecting terminal arrays being arranged along the longitudinal direction; and
  a wire having a thermal conductivity, the wire extending to the second end on the intermediate layer.

16

13. An ultrasound endoscope comprising
an ultrasound transducer configured to transmit and receive ultrasound waves,
a plurality of shield lines, and
a multilayer board comprising:
  a front-side layer;
  an intermediate layer;
  a back-side layer;
  the front-side layer, the intermediate layer, and the back-side layer being laminated in a lamination direction of the multilayer board;
  the multilayer board having a first end and a second end, the first end being one of both ends of the multilayer board in a longitudinal direction of the multilayer board among directions perpendicular to the lamination direction, the second end being another end of the both ends, the multilayer board being configured to be electrically connected to an ultrasound transducer on a side of the first end of the multilayer board;
a first ground terminal and a second ground terminal for connecting ground lines of a plurality of shield lines to be connected to the multilayer board, the first ground terminal and the second ground terminal forming a part of the front-side layer and a part of the back-side layer on a side of the second end of the multilayer board, respectively;
  a plurality of signal line connecting terminal arrays each including a plurality of signal line connecting terminals for connecting respective signal lines of the shield lines, the plurality of signal line connecting terminal arrays forming a part of the front-side layer and a part of the back-side layer in a vicinity of the ground terminal in the longitudinal direction, the plurality of signal line connecting terminal arrays being arranged along the longitudinal direction; and
a wire having a thermal conductivity, the wire extending to the second end on the intermediate layer.

* * * * *